United States Patent [19]
McClintock et al.

[11] Patent Number: 5,833,923
[45] Date of Patent: Nov. 10, 1998

[54] SAMPLING-ASSAY INTERFACE SYSTEM

[75] Inventors: Joseph A. McClintock; Mary Ann Childs; Gregory K. Shipman, all of Baltimore, Md.; William P. Trainor, Hillsboro Beach, Fla.; Erick Gray, Columbia, Md.; David Bernstein, Eldersburg, Md.

[73] Assignee: Universal Healthwatch, Inc., Columbia, Md.

[21] Appl. No.: 577,107

[22] Filed: Dec. 22, 1995

[51] Int. Cl.$^6$ .................................................. G01N 21/76
[52] U.S. Cl. .................. 422/52; 422/58; 422/61; 422/82.05; 435/287.1; 435/287.2; 435/288.7; 436/164; 436/172
[58] Field of Search ................. 422/52, 56, 57, 422/58, 61, 82.05, 82.08, 82.09; 436/165, 169, 172, 46; 435/287.1, 287.2, 287.3, 288.7

[56] References Cited

U.S. PATENT DOCUMENTS

| | | |
|---|---|---|
| 1,967,557 | 7/1934 | John . |
| 4,225,557 | 9/1980 | Hartl et al. . |
| 4,250,257 | 2/1981 | Lee et al. . |
| 4,385,113 | 5/1983 | Chappelle et al. . |
| 4,396,579 | 8/1983 | Schreoder et al. . |
| 4,719,182 | 1/1988 | Burdick et al. . |
| 4,774,192 | 9/1988 | Terminello et al. . |
| 4,803,170 | 2/1989 | Stanton et al. . |
| 4,826,772 | 5/1989 | Meathrel . |
| 4,833,088 | 5/1989 | DeSimone et al. ................... 435/287.1 |
| 4,857,453 | 8/1989 | Ullman et al. ............................ 422/56 |
| 4,861,711 | 8/1989 | Friesen et al. . |
| 4,863,689 | 9/1989 | Leong et al. . |
| 4,952,373 | 8/1990 | Sugarman et al. . |
| 4,981,653 | 1/1991 | Marino . |

(List continued on next page.)

FOREIGN PATENT DOCUMENTS

88/08534  11/1988  WIPO .

OTHER PUBLICATIONS

M. DeLuca, et al., *Factors Affecting the Kinetics of Light Emission from Crude and Purified Firely Luciferase*, Analytical Biochem, 95:194–98 (1979).

I. Johnson, *Optical Properties of Fluorescent Probes*, Part I, pp. 1–4, Molecular Probes, Inc. (date unkown).

*Phycobiliproteins and their Conjugates*, Set 14, pp. 77–79, Molecular Probes, Inc. (date unkown).

Hamamatsu Photonics K.K., Photosensor Modules H5773/H5783/H5784 Series, Technical Data (Jan. 1995).

Instruments, Test & Measuring, Keithley Electrometers, Picoammeters and Voltmeters Data (1993).

Solid State Lamps, Model 4304H6 & 4304S, Industrial Devices, (date unknown).

*Primary Examiner*—Jan Ludlow
*Attorney, Agent, or Firm*—Foley & Lardner

[57] ABSTRACT

A system and method for performing an assay for target analytes includes a sampling-device holder interface and a quantifier. The sampling device has a sampling portion and a reading portion containing a chemiluminescent reagent. The interface has a sampling-device holder and a light detector. The holder has a housing having an enclosure with a channel and a base plate with an opening. The base plate and the enclosure houses a slidable tray. The tray has a compartment adapted to seat the sampling device and an opening extending through the compartment. The reading portion is aligned with the tray opening. When the tray is closed, the tray opening is also aligned with the base plate opening, exposing the reading portion. Once the sampling portion is exposed to a sample suspected of containing the target analyte, at least one carrier liquid is introduced, if needed, to the sampling portion to transport any target analyte to the reading portion by dispersion. To measure the emitted light, the sampling device is seated into the tray. The tray is then inserted into housing. The light detector, which is connected in close proximity to the reading portion, outputs a signal. This signal is then converted to quantifiable data indicative of the target analyte quantity, using for instance, an ammeter.

9 Claims, 3 Drawing Sheets

U.S. PATENT DOCUMENTS

| | | |
|---|---|---|
| 5,037,614 | 8/1991 | Makita et al. .......................... 422/68.1 |
| 5,188,965 | 2/1993 | Wannlund . |
| 5,188,966 | 2/1993 | Eikmeier et al. . |
| 5,207,984 | 5/1993 | Kheiri . |
| 5,234,813 | 8/1993 | McGeehan et al. . |
| 5,281,395 | 1/1994 | Markart et al. . |
| 5,284,622 | 2/1994 | Krause et al. . |
| 5,290,513 | 3/1994 | Berthold et al. . |
| 5,302,348 | 4/1994 | Cusack et al. . |
| 5,354,692 | 10/1994 | Yang et al. . |
| 5,356,782 | 10/1994 | Moorman et al. . |
| 5,366,867 | 11/1994 | Kawakami et al. . |
| 5,384,264 | 1/1995 | Chen et al. . |
| 5,435,970 | 7/1995 | Mamenta et al. . |
| 5,441,698 | 8/1995 | Norell . |
| 5,504,013 | 4/1996 | Senior . |
| 5,563,042 | 10/1996 | Phillips et al. . |

SAMPLING-ASSAY INTERFACE SYSTEM

BACKGROUND

The ability to detect bacterial contamination is paramount to improving food safety. During food processing, food can become contaminated with bacteria and spoil. Food poisoning can result if food contaminated with pathogenic bacteria, or its toxic products, is ingested without proper cooking.

Standard culture plate methods for monitoring surfaces for bacterial contamination require a sterile sample collection device (generally a swab or sponge) and suitable culture media, which after inoculation, must be incubated at a controlled temperature for a minimum of several hours to days. These methods are too cumbersome and time consuming, especially if used by untrained workers. Rapid bacteria tests need to be implemented in slaughterhouses and food handling establishments to improve safety. In these establishments, one must rapidly determine whether additional cleaning is required or whether proper safety procedures have been followed. To do that, a quick, reliable bacteria measurement is needed. Unfortunately, this is often not possible because present methods require several hours or even days by trained laboratory technicians or require elaborate testing equipments that are not readily transportable to on site locations.

Attempts have been made to overcome these shortcomings with more sensitive chemiluminescence detection methods. One such chemiluminescence method measures adenosine triphosphate (ATP) to indirectly measure the bacteria content. This detection is reliable because all bacteria contain some ATP. Chemical bond energy from ATP is utilized in the chemiluminescent reaction occurring, for example, in the tails of the firefly Photinus pyralis. The mechanism of this chemiluminescence reaction has been well characterized (DeLuca, M., et al, 1979 Anal. Biochem. 95:194–198). The components of this reaction can be isolated free of ATP and subsequently used to detect ATP in other sources by a reaction that begins with formation of an enzyme bound luciferyl-adenylate complex and free inorganic pyrophosphate and ends with a rapid reaction of this complex with molecular oxygen to produce light, $CO_2$, and adenosine monophosphate (AMP).

One conventional light measuring method involves counting photons using a light reading instrument. Photographic films also have been used to monitor chemiluminescent reactions, as disclosed for example, in U.S. Pat. No. 4,396,579. A drawback of this type is that it is complex and difficult to use.

Firefly luciferin-luciferase reactions have been used for detecting microorganisms, as described in U.S. Pat. Nos. 4,385,113 and 5,366,867. These methods, however, suffer a number of deficiencies. Lyophilized luciferase-luciferin reagent is unstable at room temperature during long term storage and is unstable after liquid reconstitution over short time intervals. Additionally, after reconstitution, the reagent solution emits significant amount of light even in the absence of ATP, which decreases detection sensitivity.

The reagent instability problem was partly addressed by drying luciferin-luciferase reagents separately onto plastic surfaces. But this requires an additional step of transferring microorganisms from a collection device to a plastic surface, increasing complexity. Further, while this solves the instability problem, it unfortunately lowers the detection sensitivity and creates a new problem—incomplete ATP transfer from the collection device to a separate plastic surface containing the luciferase-luciferin reagent. Furthermore, this solution introduces a new time variable between the transfer and the light emission measurement.

Adding reagent at timed intervals causes additional problems because the light emission kinetics become shorter as the light intensity decreases. The twin timing and reagent instability problems also plague other chemiluminescence chemistries that have been developed to detect target analytes. For example, U.S. Pat. No. 4,396,579 describes a complicated, expensive automated machine designed to add chemiluminescent reagent at fixed time intervals to overcome the light emission kinetic problem. The reagent instability and the timing problems make this machine unusually complex.

Thus, there is a need for an assay device that benefits from high sensitivity and speed of chemiluminescence detection, but one that excludes the aforementioned complexity, timing, reagent instability, and high background light emission problems. Copending U.S. patent application Ser. No. 08/560,094, filed Nov. 17, 1995, (hereafter "the copending application"), entitled *CHEMILUMINESCENT ASSAY METHODS AND DEVICES FOR DETECTING TARGET ANALYTES*, describes chemiluminescent assay methods and devices that fulfill this need. The disclosure of the copending application is incorporated herein by reference.

The copending application discloses a simple, easy to use chemiluminescent sampling assay device that eliminates or reduces the complexity associated with manually measuring and adding reagent at timed intervals. This sampling device also provides means to measure light intensity and allows rapid analysis of target analytes at the sample site. Specifically, it comprises a container or envelope holding a sampling strip having separate sampling and reagent portions. The reagent portion contains one or more dried chemiluminescent reagents. The device has a light-permeable portion that permits light generated by a chemiluminescent reaction within the sampling strip to exit the container. This sampling device eliminates or reduces much of the complexity associated with other known assay methods and, as a result, decreases the cost and training requirements for detecting target analytes. A wide range of target analytes can be detected by this device. In fact, the sampling portion of the device can collect virtually any type of target analyte, not only from physical contact with a solid, but also from sample liquid applied or introduced thereto.

In use, the sampling portion of the sampling device receives a sample, for example, by wiping the sampling portion over a surface suspected of containing the target analyte. A carrier liquid is then added to the sampling area, if needed, which liquid transports the target analyte into the reagent portion. The carrier liquid also re-wets chemiluminescence reaction components located in the reagent portion, and thus allows a chemiluminescence reaction to begin. The instability problem suffered by prior art methods is overcome by providing the chemiluminescent reagent in a dried state within the reagent portion. A bacteriolytic agent (e.g., a detergent) in the carrier liquid lyses bacteria that have been collected in the sampling portion. ATP liberated by lysis of bacteria then participates in a luciferase reaction to produce light. The advantage of rapid and sensitive detection of bacteria can be realized through sensitive light detection using, for example, a photomultiplier. The copending application discloses, in essence, a compact, self-contained assay device that allows light detection using any of known light detection methods, including an optical observation.

Conventional instruments for measuring chemiluminescence, including luminometers and fluorometers, however, are not particularly suited for such an assay device that has a flat geometry. To this end, there is a need for a portable interface readily interfaceable with a photomultiplier or other known light detector to provide a simple, efficient light intensity reading from the sampling assay device of the type disclosed in the copending application.

The present inventors have discovered such an interface, along with other advantageous improvements associated therewith.

SUMMARY

The present invention is drawn to a sampling-device holder, a sampling-device holder interface, a system thereof, and a method for performing an assay for a target analyte from a sampling device. According to the present invention, the sampling device has a container and a sampling strip inside the container. The sampling strip has a sampling portion for introducing a sample, a reading portion containing a reagent for producing chemiluminescent reaction with the target analytes, and a transfer portion connecting the sampling and reading portions for transferring the sample from the sampling portion to the reading portion. The container has an opening to permit introduction of samples to the sampling portion. It also has a light transmissive portion, such as a window or opening, visibly exposing the reading portion.

According to the present invention, the holder includes a housing and a tray. The housing has at least first and second walls forming a cavity therebetween. One of the first and second walls has an opening or light transmissive window. The tray is received in the cavity and movable between opened and closed positions. The tray has a compartment adapted to seat and support the sampling assay device. The first opening is in registry with the reading portion when the tray is in the closed position to enable observation of the reading portion through the first opening.

The second wall preferably is an enclosure having a channel and the first wall preferably is a base plate connected to the enclosure, the channel defining the cavity. The tray has a second opening (or light transmissive window) extending through the compartment, which opening is in registry with the reading portion of the seated sampling device. The second opening is in registry with the first opening when the tray is in the closed position to enable observation of the reading portion through both the first and second openings. When the tray is in the opened position, the tray blocks the first opening. The tray, which is slidable between the opened and closed positions, preferably includes a handle to accommodate pulling and pushing actions.

The tray also includes a pair of parallel slots. These slots are adapted to be occupied by fasteners that hold the holder together. Fasteners are spaced along each slot. Because the slots are closed at both ends, the length thereof less the spacing between the fasteners occupying the same slot defines the distance the tray can slide within.

To further maintain the assay device flat against the bottom wall of the compartment, a cover dimensioned to seat inside the compartment is preferably included. This cover shields at least the reading portion of the seated sampling device.

The interface for measuring light intensity generated by a sampling assay device according to the present invention uses the housing defined above and a light detector—means for converting light generated from the sampling device to an output signal corresponding to the amount or intensity of the light generated, such as a photomultiplier—which can be connected to a quantifier for quantifying the light intensity. The light detector, which has a light gathering window for collecting light is connected to the present sample holder. The light detector is preferably connected to the first wall so that the window is aligned with the first opening.

The system according to the present invention for measuring light intensity generated by target analytes contained in a sample comprises the sampling assay device and the interface defined above, and includes a quantifier—means for converting the output signal to quantifiable data indicative of the amount of the target analytes—connected to the light detector.

The method of performing an assay for a target analyte, according to the present invention involves use of the sampling assay device defined above. Using the present sampling device, the sampling portion is exposed to a sample suspected of containing the target analyte. At least one carrier liquid is introduced, if needed, to transport any target analyte from the sampling portion to the reading portion. The carrier liquid, if needed, preferably includes a target analyte extraction reagent that extracts target analyte present in the sampling portion. Thereupon, the light emitted by the reading portion is detected.

To quantify the amount of light, the sampled sampling assay device is seated into a tray. The tray is then inserted into a light-tight housing, but is provided with a light transmissive window in the housing to expose the reading portion. The amount or intensity of light from the reading portion is then read or measured using a light detector connected in close proximity to the reading portion. The output is then converted to quantifiable data indicative of the amount of the target analyte using a quantifier connected to the light detector.

DETAILED DESCRIPTION OF THE DRAWINGS

Figure 1:
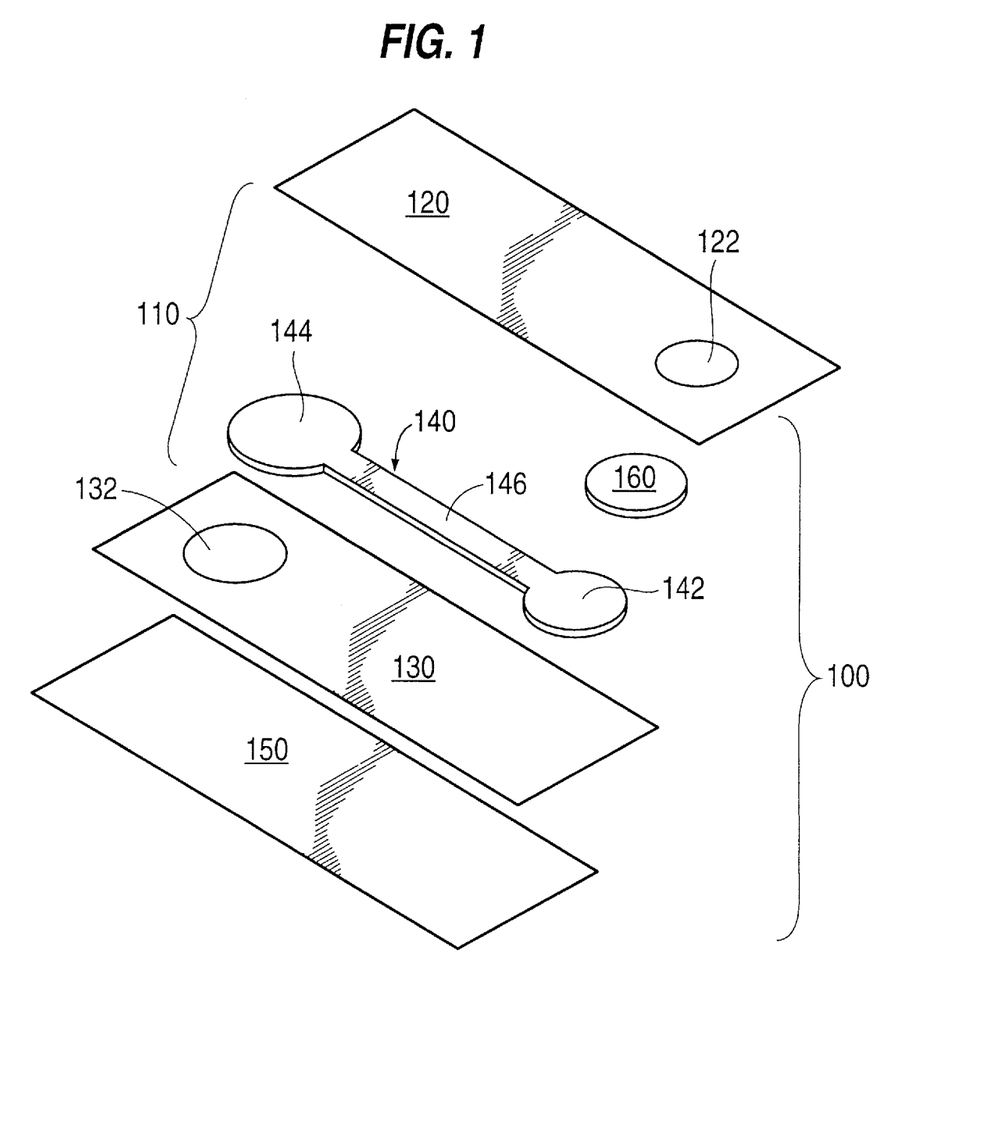
FIG. 1 is an exploded view of a sampling assay device according to the present invention.

FIG. 1 illustrates a sampling assay device 100 presently contemplated for use with the present interface 10. This device 100 includes a container or envelope 110 for containing a sampling strip 140, which has a sampling portion 142 for receiving a sample, a reading portion 144 for detecting light, and a transfer portion 146 connecting the sampling portion to the reading portion to enable a sample to travel from the sampling portion to reading portion. The housing envelope 110 comprises a top layer 120 and a bottom layer 130, each having an opening 122, 132 in alignment respectively with the sampling and reading portions 142, 144, exposing these portions. Each of the top and bottom layers 120, 130 is preferably composed of a thin liquid impervious material, such as a plastic film. The sampling strip 140 is sandwiched and retained between the top and bottom layers 120, 130. These top and bottom layers can be sealingly joined together, for example, by heat, adhesive, ultrasonic welds, or any physical means that retain layers together while retaining the sampling strip fixedly in place. A single film sheet can also be folded to form the upper and lower layers. Alternatively, an envelope with three sides already sealed can also be used.

The bottom layer 130 preferably includes a sealing film 150 positioned underneath as shown in FIG. 1. This film 150 is preferably light transmissive (clear) to transmit chemiluminescent light emitting from the sampling portion. The film 150, however, could be structured so that only the region directly below the bottom layer opening 132 is clear. Although FIG. 1 shows the film 150 positioned below the bottom layer, it can also be positioned above the bottom layer, below the sampling strip. The sealing film 150 can be omitted altogether if the bottom layer, at least the portion below and in registry with the reading portion 144, is formed of a clear material to provide a window for the reading portion. In this regard, the entire bottom layer could be made of a clear material if desired. Even just the opening 132 could be covered with a light transmissive material, either above or below the bottom layer 130. The sampling portion 140 is positioned directly under the top-layer opening 122, sandwiched between the top layer 120 and the bottom layer 130. In the embodiment shown, a sample collecting member 160 is sandwiched between the top layer 120 and the sampling portion 142, with the collecting member exposed to the top layer opening 122. The sampling portion is thus accessible through the envelope 110. The collecting member is preferably adsorbent, which is preferably composed of fibrous material, such as glass fiber, cotton, dacron, or paper, and it may be porous, such as porous polyethylene or sintered glass.

The sampling strip 140 is also composed of an adsorbent material, which may be fibrous, such as glass fiber, cotton, dacron, or paper and the like, and it may be porous, such as porous polyethylene or sintered glass and the like. An ordinary artisan will recognize many useful materials, such as those used in chromatographic-type assays currently available. The sampling and reading portions 142, 144 are preferably wider than the transfer portion 146 connecting these wider portions, although many other configurations are possible. The sampling and reading portions can come in various shapes, including circular, rectangular, or triangular. The shape can be maximized for diffusion and reagent mixing. Because the sampling and reading portions have larger surface areas, they advantageously allow a maximum surface-area exposure to a light detector.

The sample collecting member 160 is preferably in physical contact with the sampling portion to maximize liquid transfer thereto. The reading portion, where the chemiluminescent reaction is designed to occur, contains one or more chemiluminescent reagents, preferably in a dried form. Additionally, the reading portion can contain other reagents useful for the assay including, for example, the detergent or other bacteriolytic reagent for extracting ATP from bacteria.

A wide variety of chemiluminescent chemistries can be used with the present sampling assay device. Acceptable chemiluminescence chemistries include, among others, the reaction of hydrogen peroxide with horseradish peroxidase labelled antibodies and luminol, enhanced horseradish peroxidase, reactions that include the use of diacylhydrazides, acridinium salts, dioxitanes, and bioluminescent reactions involving cofactors, such as reduced nicotine adenine dinucleotide in the case of marine bacteria. A particularly preferred chemiluminescent chemistry is the firefly ATP assay, which utilizes luciferase and at least one cofactor to generate light from ATP.

At least one chemiluminescent reaction reagent is present in the reading portion 144, preferably in a dry state. When preparing the reading portion, reagents may be conveniently applied as a solution and then dried or they may be applied in a dry form, such as a powder or suspension in an organic solvent or slurry. Other methods are known in the art and the preferred one can be determined by characteristics of the reaction components desired.

Additionally, carrier liquid stored in a reservoir (not shown) can be used, as described in the aforementioned copending application. Specifically, the reservoir can be hinged to the envelope 110, adjacent to the sample collecting member 160 so that it can be movably positioned into the member 160. After sampling the target analyte, the reservoir can be directed over the sampling portion, whereupon the reservoir then can be broken (by a finger pressure for example) so that the carrier liquid contained therein is released directly over the sampling portion. In that embodiment, no separate solution is needed as all ingredients are present in the sampling assay device. The carrier liquid preferably includes a bacteriolytic agent that releases ATP from any bacteria present in the sampling portion. Acceptable carrier liquids include, among others, a buffer solution or a buffer solution with detergent. Buffer solutions of TRIS, HEPES buffers at pH 7.0 to 9.0, and most preferably HEPES buffer at 7.8 with EDTA are preferred when used with firefly luciferase from *Photinus pyralis*. EDTA is a preferred ingredient because ATP degrading enzymes require divalent metal cations for activity and EDTA chelates these. Detergent, which can also be present in the sampling or reading portion or included with the carrier, dissolves in liquid added to the sampling device and serves to open cells and liberate cell components. Several suitable detergents or combination of detergents are known to those skilled in the art and include, nonionic detergents such as Triton X-100, Nonidet P40, n-Undecyl Beta-D glucopyranoside, Zwitterionic detergents such as n-hexadecyl-N,N-dimethyl-3-ammonio-1-propanesulfonate, and cationic detergents such as alkyltri-methylammonium bromides, benzalkonium chloride, cetyl dimethyl-ethyl ammonium bromide, dodecyltrimethyl-ammonium bromide, and cetyltrimethylammonium bromide. The concentration of detergent solution varies for each type of detergent and can range from 0.1% to 6%, and preferably from 0.5% to 2.0%.

Devices for detecting intensity of chemiluminescent light are generally known. The present interface is adapted to provide a simple way of interfacing the sampling assay device to such detecting devices. Chemiluminescent light, for instance, can be detected electronically by, for example, a photomultiplier, photo diode, photofet or charge coupled device. The most preferred is a photomultiplier because of its sensitivity. The interface 10 according to the present invention provides a simple way of interfacing the sampling device 100 to a photomultiplier 50. One known photomultiplier is disclosed in HAMAMATSU PHOTONICS K.K., Photosensor Modules H5773/H5783/H5784 Series, Technical Data, January 1995, the disclosure of which is incorporated herein by reference. The photomultiplier 50 can be, for instance, Module H5773, a schematic functional diagram of which is illustrated in FIG. 2A.

Figure 2:
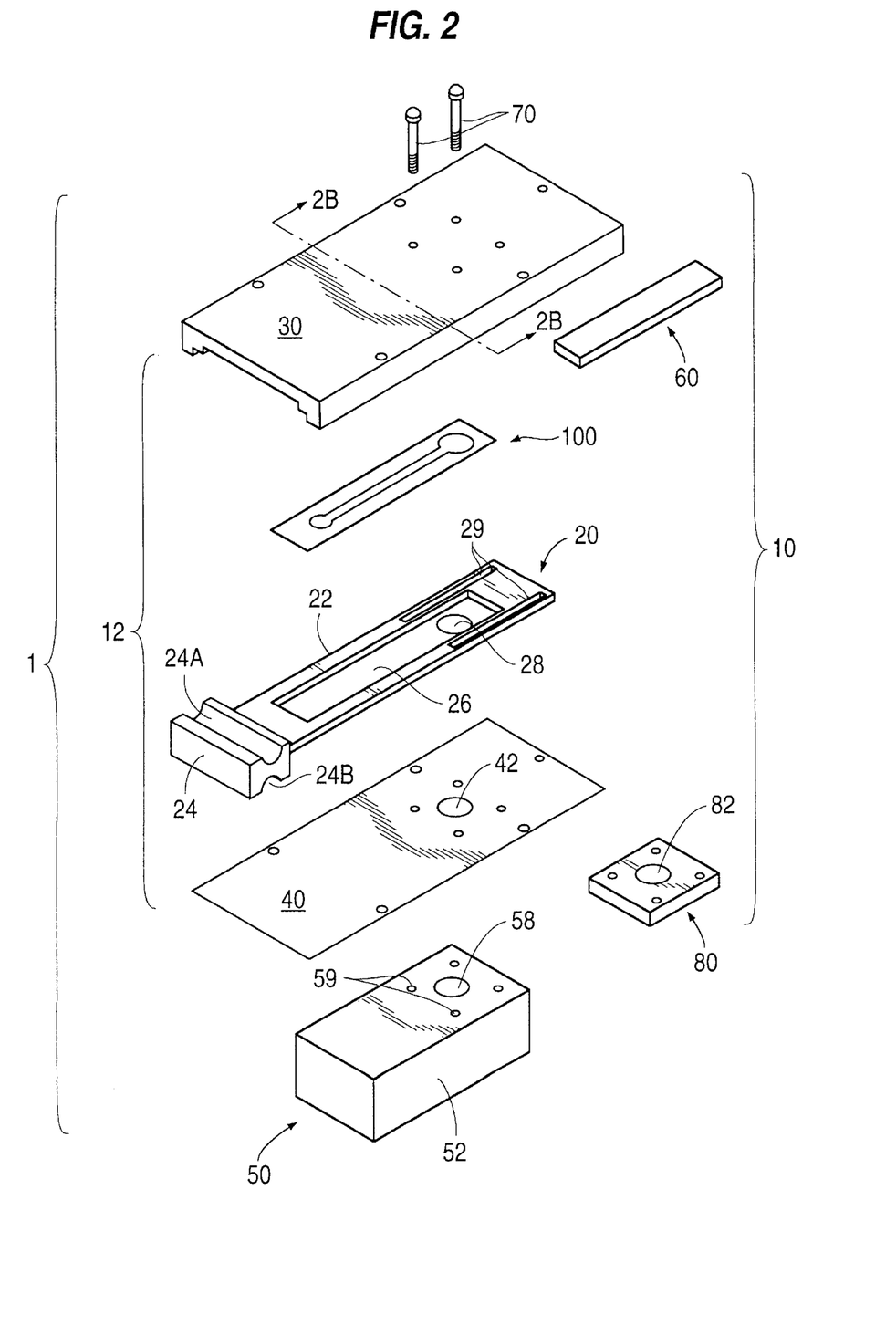
FIG. 2 is an exploded view of a sample interface according to the present invention.
Figure 2A:
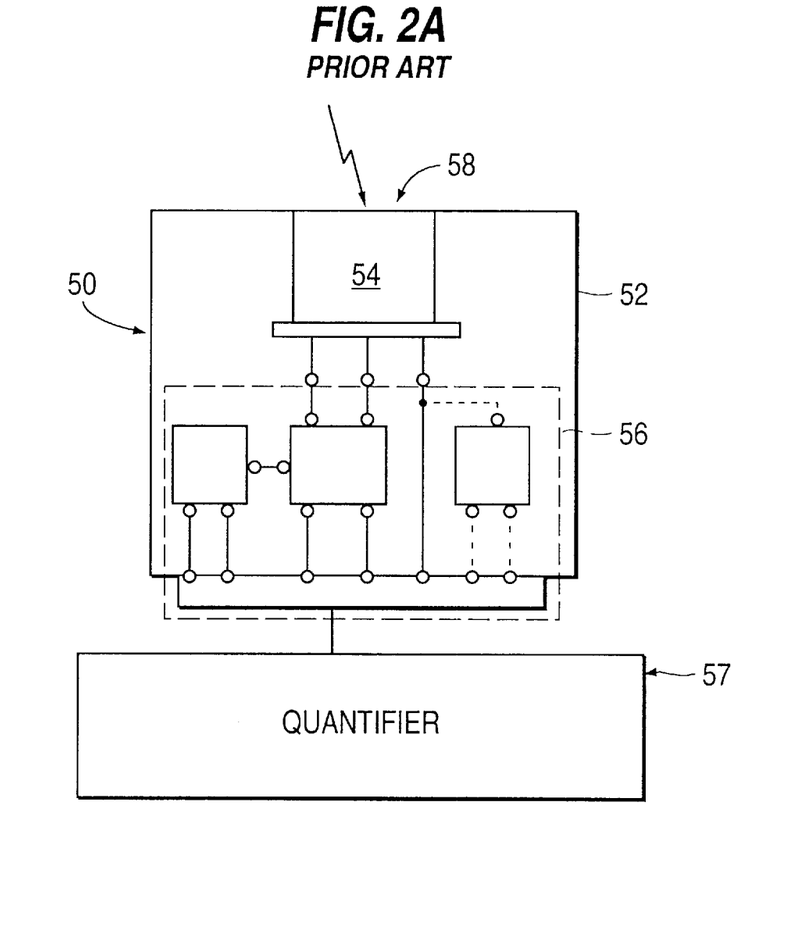
FIG. 2A is a schematic diagram of a known photodetector or photomultiplier connected to a conventional quantifier (ammeter).

As shown in FIG. 2, the present interface 1 comprises a sampling-device holder 10 connected to a photomultiplier 50. The holder 10 has a housing 12 comprising an enclosure 30 and a base plate 40. The holder also includes a movable tray 20 for seating the sampling device 100. Although FIG. 2 shows the housing 12 in two separate pieces, it could be also formed of a single molded or machined piece, if desired. The tray 20 has a generally flat plate-like body 22 and a handle 24. The flat body 22 has a blind-recess or well 26 (having a bottom) forming a compartment for flatly supporting and seating the sampling device 100. The height or depth of the well is greater than the thickness of the sampling device 100 to maintain the device 100 inside within the well 26 so that no part of the enclosure contacts the device 100. In this regard, a flat sample cover 60 can be positioned over the sample to maintain the sampling device in a flat condition. The sample cover 60 is configured and dimensioned to fit inside the well and placed over at least the reading portion 144. The cover provides a dual purpose of preventing light seepage into the sampling device and flatly seating the sampling device. The cover 60 is preferably shorter than the length of the sampling device 100 so that it does not cover the sampling portion 142 to prevent cross contamination between samples. The combined thickness between the cover 60 and the sampling device 100 should not exceed the depth of the well 26.

An opening 28 is formed through the flat body 22 adjacent the distal end of the well 26. When the sampling device is seated in the well and the distal end of the sampling device 100 abuts against distal end of the well 26, the opening 28 registers in alignment with the reading portion 144 and the bottom-layer opening 132 so that light emitting from the reading portion passes therethrough. The flat body 22 further includes a pair of parallel, longitudinal guiding slots 29, which provide two discrete functions. First, they permit complete passage of fasteners 70, such as bolts or the like, which maintain the present interface 1 together. Second, these slots (with the fasteners acting as a stop) enable the tray to slide by a predetermined length equalling the slot length less the distance between the fasteners passing through the same slot. In other words, the slot limits the movement of the tray, while maintaining the tray connected to the enclosure. The tray thus cannot be pulled out completely without removing the fasteners 70.

The handle 24 has upper and lower contoured recesses 24A, 24B to provide more ergonomical gripping surfaces. The junction at the handle and the flat body preferably should be carefully configured and dimensioned to provide a light-tight seal against the ends of the enclosure 30 and the base plate 40. The tray also serves as a shutter, automatically blocking the photomultiplier reading window 58 when the tray is opened, and opening the reading window 58 when it is closed.

Figure 2B:
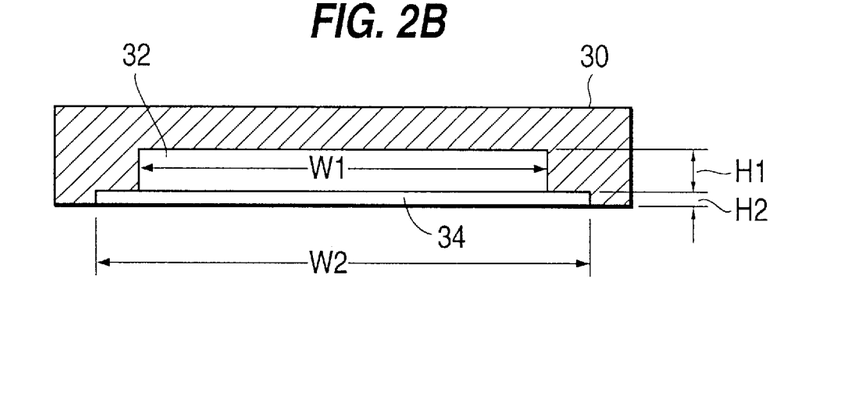
FIG. 2B is a cross-sectional view of the enclosure taken along line 2B—2B of FIG. 2.

FIG. 2B shows a cross-sectional view of the enclosure 30. The base plate 40 and the enclosure 30, which constitute the first and second walls, define a cavity or space to which the tray is inserted. The enclosure is substantially rectangular as shown, although other configurations can be contemplated. The enclosure 30 has a first channel 32 configured and dimensioned to closely fit against the flat body 22. Specifically, the channel 32 has a width W1 and a height H1, substantially the same as the width and height of the flat body 22, only slightly larger to allow the flat body to slide against the side walls of the first channel 32. The tight tolerance is designed to prevent light seepage into the well 26. Alternatively, seals can be placed to block out light. The enclosure also has a second wider channel 34 contiguous with the first channel 32. Specifically, the first channel is above the second channel. This second channel 34 has a second width W2 and a second height H2 (and a length) substantially identical as those of the base plate 40, which occupies the second channel when assembled. Again, a tight tolerance is desirable to prevent light seepage between the enclosure 30 and the base plate 40.

The base plate 40 also has an opening 42, which when assembled with the enclosure 30 and the tray 20, will be in registered alignment with the tray opening 28 to enable light to pass therethrough.

Referring to FIG. 2A, the photomultiplier 50, such as the one disclosed in the aforementioned HAMAMATSU publication, has a housing 52 encasing a phototube 54 and an associated circuitry 56 for outputting a signal correlating to the light intensity detected. The photomultiplier can be connected to a conventional light intensity quantifier 57, such as a KEITHLEY Model 485 Picoammeter (ammeter), which measures low current in the range between 100 fA to 2 mA. The phototube is accessed through the opening 58 formed in the housing 52. The present invention provides a simple, easy to use interface for reading light intensity from the sampling device. The photomultiplier 50, such as the one disclosed in the aforementioned HAMAMATSU publication, has four threaded mounting holes 59. In this regard, the enclosure 30 and the base plate 40 preferably have the same mounting hole pattern for permitting passage of the fasteners 70 (only two shown), such, as bolts and screws, so that the holder 10 can be directly mounted to the photomultiplier 50.

The light intensity emitted from the chemiluminescent reaction obeys an inverse square relationship to distance following Lambert's Law. Therefore, if a light detector is used, detection sensitivity is optimized by placing the detector as closely as possible to the reading portion 144. The interface 1 according to the present invention enables that, maximizing the collected light and measurement sensitivity by directly connecting the holder 10 to the photomultiplier 50 to provide a shortest direct optical path. The present inventors have found that the photomultiplier 50, such as the ones disclosed in the aforementioned HAMAMATSU publication has a slight depression around the hole pattern. In this situation, a spacer 80 having an opening 82 in registry with the window 58 and the same bolting pattern can be used. The spacer can also be used as an optical filter holder if it is desired to limit the photomultiplier spectral response. This spacer 80 is generally needed when the photomultiplier does not provide a flat planar mounting surface or when a filter contained therein is desired to enhance measurement sensitivity.

The firefly luciferase from *Photinus pyralis* is 62,000 daltons and catalytically active in its monomeric form. The firefly luciferase reaction has a quantum yield of 0.88, which is the highest efficiency for any known bioluminescent reaction. At the optimum reaction pH of 7.8, the light emission is 562 nm. As the pH shifts to acidic conditions, the light emission has a second peak at 616 nm, which increases in intensity while the 562 nm peak decreases. The pH of the reaction determines the ratio of the 562 nm peak to the 616 nm peak. At pH 5.4, the 616 nm peak is at a maximum and there is no 562 nm peak. The emission spectra change with pH due to the protonation of the oxy luciferin molecule (the light emitter). Oxyluciferin as a dianion emits a yellow-green light (562 nm) and as a monoanion it emits a red light (616 nm).

Photomultiplier, such as the HAMAMATSU Module H5773/H5783/H5784 Series photosensors, have a highest spectral response between 400 and 500 nm, with decreasing responses above and below. Thus, the spectral response is greater at 562 nm than at 616 nm. In this regard, it would be desirable to run the luciferase assay at 7.8 pH to ensure a higher efficiency at the 562 nm peak emission. A filter can also be provided to block out a certain range of spectra to enhance detection.

In operation, the sampling device 100 preferably comes packaged in another sealed container or envelope (not shown). Once the sampling device 100 is taken out, sampling can begin. The sample collecting member 160 is exposed to the target area, for instance, by contacting or swabbing the suspected surface, liquid, or other area suspected of containing the analyte with the member 160. Alternatively, the sample to be tested can be directly introduced to the sample collecting member 160. Then, carrier liquid is introduced to the member, if needed, to wet the target analyte and move, by a wicking action or diffusion, any analyte present to the reading portion where one or more dried chemiluminescent reagents are present. If the target analyte to be tested is in a liquid form, then the carrier liquid may not be necessary. Finally, the degree of chemiluminescence light produced in response to the presence of target analyte in the sample is detected, where the degree correlates to the amount of the analyte present.

A target analyte as used herein, is a molecule such as a protein, cell metabolite or microorganism such as a prokaryotic cell, virus, microplasma or free living eukaryotic cell. The target analyte can be introduced by physical contact such as by swabbing a suspected contaminated surface with the device or by introducing the sample in liquid form by, for example, an eye dropper or other dispenser, or by brief immersion of the device in the liquid to be tested.

If wiping or swabbing is carried out, then finger pressure is preferably placed on the bottom layer 130, behind the opening 122 to more fully expose the sample collecting member 160 to the sample. The applied carrier liquid diffuses through the adsorbent sampling strip, where it, upon reaching the reading portion, rehydrates the dried chemiluminescent reagent contained therein. Any ATP present in the carrier liquid reacts with the rehydrated chemiluminescent reagent present in the reading portion to emit light.

Once the sampling has been made, the sampling device 100 is positioned on the tray 20, with the distal edge of the device 100 abutting the distal wall of the well 26, where the reading portion will be in registry with the opening 28. The cover 60, if used, is placed over at least the reading portion 144 to prevent light seepage therein. Thereafter, the tray is closed, which seals the sampling device against any light seepage, but registering the reading portion with the window opening 58 of the light detector 50, such as a photomultiplier. Any light emitted by the reading portion in response to the ATP reaction is measured by the light detector 50. Since it may take time for the analyte to travel to the reading portion and react with the reagent present therein, it would be desirable to monitor the reading portion over a predetermined period to observe a peak reading. This measurement can be quantified by converting its output signal to quantifiable data indicative of the amount of the target analyte present.

Given the disclosure of the present invention, one versed in the art would readily appreciate that there may be other embodiments and modifications well within the scope and spirit of the present invention. Accordingly, all expedient modifications readily attainable by one versed in the art from the present disclosure within the scope and spirit of the present invention are to be included as further embodiments of the present invention. For example, the sample cover 60 can be attached to a spring-loaded hinge that would automatically open and close in response to the tray opening or closing, respectively. To further prevent possible cross-contamination between samples, the well could be made deeper toward the sampling portion. Alternatively, the holder could also be provided with a sharp blade for cutting-off at least the sampling portion. This would prevent further possible sampling due to cross-contamination. Alternatively, the sampling portion could be cut-off before inserting to the tray.

If the photomultiplier has its phototube extending outwardly, raised above the housing 52, the base plate 140 would have an opening just large enough to insert the phototube through the base plate 140, with the phototube end flush with the upper base plate surface, immediately below the tray flat base 22 to achieve the shortest optical path from the reading portion to the phototube. of course, a tight tolerance or some other means of preventing light seepage would be necessary.

Accordingly, the scope of the present invention accordingly is to be defined as set forth in the appended claims.

What is claimed is:

1. A system for measuring light intensity generated by target analytes contained in a sample, comprising:

a) a sampling assay device comprising:
   a container;
   a sampling strip having a sampling portion for introducing the sample, a reading portion containing a reagent for producing chemiluminescent reaction with the target analytes, and a transfer portion connecting the sampling and reading portions for permitting transfer of the sample from the sampling portion to the reading portion, the sampling strip being inside the container,
   wherein the container has means to permit introduction of the sample to the sampling portion and a light transmissive portion exposing the reading portion;

b) a sample holder adapted to encase the sampling strip therein comprising:
   a housing having a first wall and a second wall, the first and second walls forming a cavity therebetween, the first wall having a first opening; and
   a tray received in the cavity and movable between an opened position and a closed position, the tray having a compartment adapted to receive and support the sampling assay device,
   wherein the first opening is in registry with the reading portion when the tray is in the closed position to enable observation of the reading portion through the first opening;

c) a light detector for converting light generated from the sampling device to an output signal corresponding to the amount or intensity of the light generated, the light detector having a light gathering window, wherein the light detector is connected to the first wall so that the window is aligned with the first opening; and d) a quantifier for converting the output signal to quantifiable data indicative of the amount of the target analytes.

2. A system according to claim 1, where the light detector is a photomultiplier.

3. A system according to claim 1, wherein the quantifier is an ammeter.

4. A system according to claim 1, wherein the tray is slidable between the opened and closed positions.

5. A system according to claim 4, wherein the tray includes a pair of parallel slots, wherein the slots are occupied by fasteners spaced along the slots, and wherein the length of the slot less the spacing between the fasteners occupying the same slot defines the amount of the tray sliding movement.

6. A system according to claim 1, wherein the second wall is an enclosure having a channel and the first wall is a base plate connected to the enclosure, the channel defining the cavity.

7. A system according to claim 6, wherein the tray has a second opening extending through the compartment, wherein the second opening is in registry with the reading portion when the sampling device is seated in the compartment and is in registry with the first opening when the tray is in the closed position to enable observation of the reading portion through the first and second openings, and wherein the tray blocks the first opening when the tray is in the opened position.

8. A system according to claim 7, further comprising a cover dimensioned to seat inside the compartment and adapted to cover at least the reading portion of the sampling strip sitting in the compartment.

9. A system for measuring light intensity generated by target analytes contained in a sample, comprising:
 a) a sampling assay device comprising:
  a container;
  a sampling strip having a sampling portion for introducing the sample, a reading portion containing a reagent for producing chemiluminescent reaction with the target analytes, and a transfer portion connecting the sampling and reading portions for permitting transfer of the sample from the sampling portion to the reading portion, the sampling strip being inside the container,
  wherein the container has an opening to permit introduction of the sample to the sampling portion and a light transmissive portion exposing the reading portion;
 b) a sample holder comprising:
  a housing having a first wall and a second wall, the first and second walls forming a cavity therebetween, the first wall having a first opening; and
  a tray received in the cavity and movable between an opened position and a closed position, the tray having a compartment adapted to receive and support the sampling assay device, and a second opening extending through the compartment,
  wherein the first opening is in registry with the reading portion when the tray is in the closed position to enable observation of the reading portion through the first opening,
  wherein the second opening is in registry with the reading portion when the sampling device is seated in the compartment and is in registry with the first opening when the tray is in the closed position to enable observation of the reading portion through the first and second openings, and
  wherein the tray blocks the first opening when the tray is in the opened position;
 c) a light detector for converting light generated from the sampling device to an output signal corresponding to the amount or intensity of the light generated, the light detector having a light gathering window, wherein the light detector is connected to the first wall so that the window is aligned with the first opening; and
 d) a quantifier for converting the output signal to quantifiable data indicative of the amount of the target analytes.

* * * * *